United States Patent
van der Geest et al.

(10) Patent No.: US 6,772,082 B2
(45) Date of Patent: Aug. 3, 2004

(54) METHOD FOR DETECTING AND CORRECTING SENSOR FAILURE IN OIL AND GAS PRODUCTION SYSTEM

(75) Inventors: Robert Anton Bernard van der Geest, Oslo (NO); John Allen, Houston, TX (US); Svein Arne Morud, Bekkestua (NO); Bjorn Oyvind Bringedal, Oslo (NO)

(73) Assignee: ABB AS (NO)

( * ) Notice: Subject to any disclaimer, the term of this patent is extended or adjusted under 35 U.S.C. 154(b) by 113 days.

(21) Appl. No.: 10/133,783

(22) Filed: Apr. 26, 2002

(65) Prior Publication Data

US 2003/0005747 A1 Jan. 9, 2003

Related U.S. Application Data

(60) Provisional application No. 60/286,600, filed on Apr. 26, 2001.

(51) Int. Cl.[7] ............................................... G01F 25/00
(52) U.S. Cl. ........................................ 702/116; 73/1.34
(58) Field of Search ................................ 702/116, 100, 702/34, 104; 73/1.34

(56) References Cited

U.S. PATENT DOCUMENTS

| | | | |
|---|---|---|---|
| 4,576,043 A | 3/1986 | Nguyen | 73/195 |
| 4,604,902 A | 8/1986 | Sabin et al. | 73/861.04 |
| 4,974,446 A | 12/1990 | Vigneaux | 73/861.04 X |
| 5,361,206 A | 11/1994 | Tabeling et al. | |
| 5,597,042 A | 1/1997 | Tubel et al. | 166/250.01 |
| 5,966,311 A | * 10/1999 | Stemporzewski, Jr. et al. | 702/116 X |
| 6,453,279 B1 | * 9/2002 | Prasad et al. | 702/116 X |
| 6,510,397 B1 | * 1/2003 | Choe | 702/116 |

FOREIGN PATENT DOCUMENTS

| | | |
|---|---|---|
| EP | 0 314 654 B1 | 1/1992 |
| GB | 2 186 809 A | 8/1987 |
| WO | WO 01/22041 A1 | 3/2001 |

* cited by examiner

Primary Examiner—Thomas P. Noland
(74) Attorney, Agent, or Firm—Michael M. Rickin, Esq.

(57) ABSTRACT

Sensor failure in an oil and gas production system is monitored and detected by checking the consistency of the measurements of the sensor in question using a computer-based process model with the measurements of the other sensors in the system. The present invention also generates a back-up value for a failing sensor with the process model by identifying the value that is most consistent with the measurements of the other sensors in the system.

22 Claims, 5 Drawing Sheets

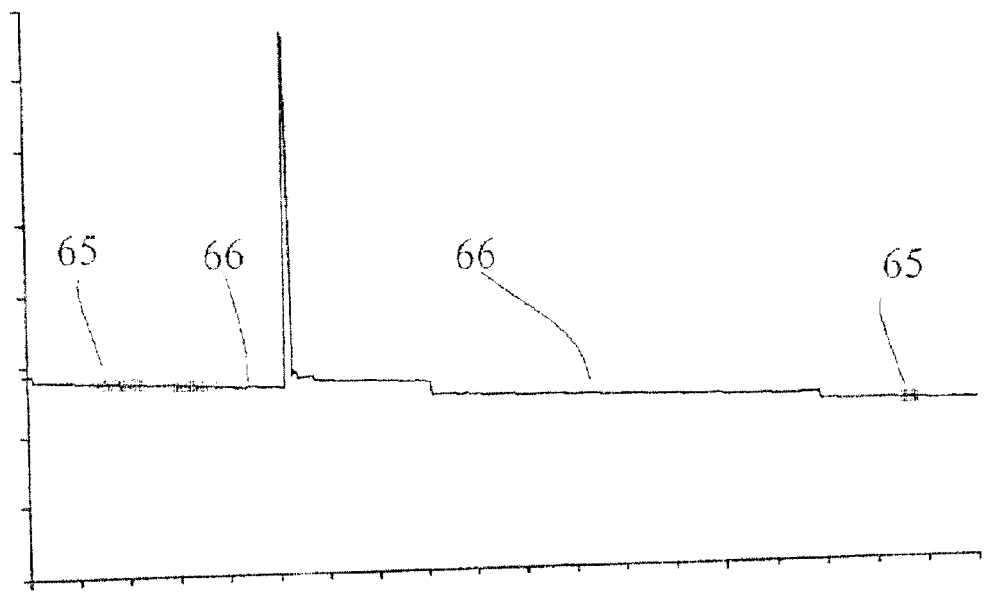
Fig. 4 Production data
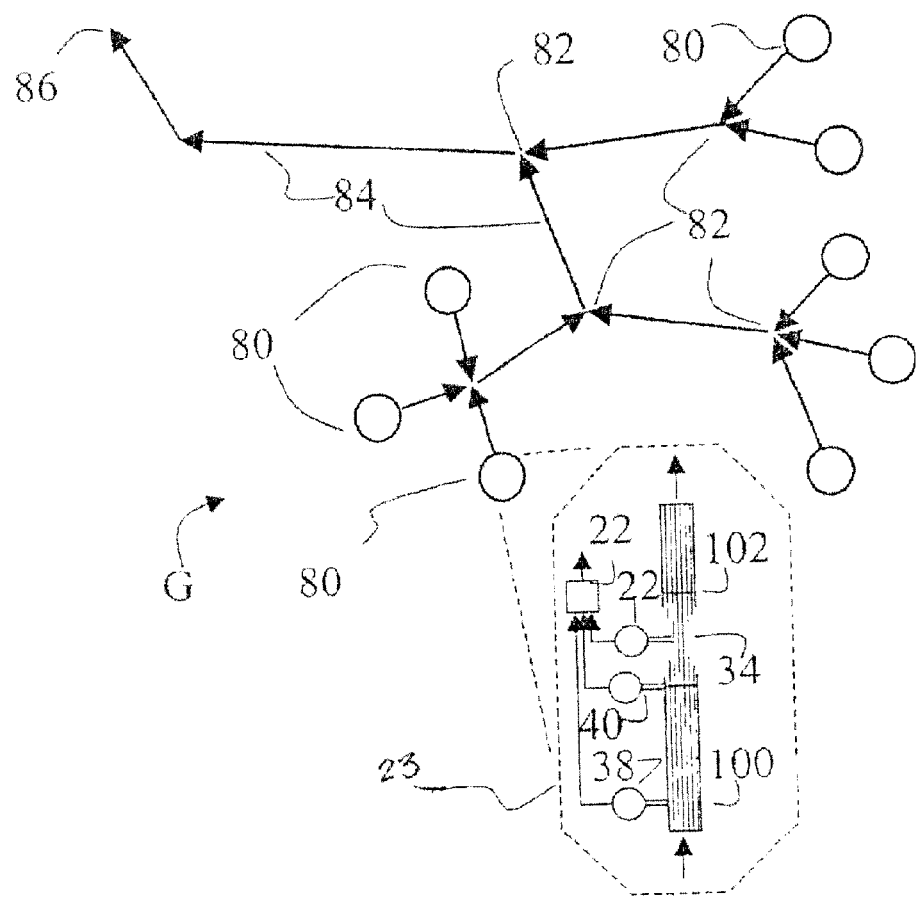
Fig. 5

METHOD FOR DETECTING AND CORRECTING SENSOR FAILURE IN OIL AND GAS PRODUCTION SYSTEM

CROSS REFERENCE TO RELATED APPLICATION

This application claims the priority of U.S. provisional patent application Ser. No. 60/286,600 filed on Apr. 26, 2001, entitled "Method For Detecting And Correcting Sensor Failure In Oil And Gas Production System" the contents of which are relied upon and incorporated herein by reference in their entirety, and the benefit of priority under 35 U.S.C. 119(e) is hereby claimed.

BACKGROUND OF INVENTION

1. Field of Invention

The present invention relates to production systems for the production of oil and gas, and in particular to the validation of sensors installed in such systems for measuring physical properties of the flow through the production system.

2. Description of the Prior Art

Oil and gas production systems typically contain sensors for measuring physical properties of the flow. Sensor measurements in the production system are for instance used as input (initial values) for simulations of the reservoir.

A well-known problem in the oil industry is that sensors in the production system become inaccurate, or even fail completely, after some time in operation. The problems are mainly due to the harsh conditions under which such equipment is operated, such as the high pressure, the high temperature, or the corrosive environment present in the production system.

New oil wells are being equipped with sensors increasingly often. An example of a sensor that is being used in an oil and gas production system is a venturi down-hole flow meter. A venturi down-hole flow meter is a sensor which in itself comprises several sensors such as pressure sensors. It is getting more and more common to install venturi down-hole flow meters in new wells. Venturi down-hole flow meters feed other parts of the production system with essential information: the values from venturi down-hole flow meters are essential for critical functions such as well allocation.

An example of a flow meter based on a process model of an oil well implemented in a data processing system is the software product Wellocate™ (currently known as OptimizeIT Well Monitoring System) supplied by ABB AS of Billingstad, Norway, the assignee of the present application. A paper, "Oil Well Allocation: the Ultimate Interpolation Problem" (L. T. Biegler, A. Bramilla, C. Scali, G. Marchetti (editors), Advanced Control of Chemical Processes 2000, Elsevier, 2001) describes how Wellocate™ identifies the flow rate in an oil well by checking the consistency of an assumed flow rate with the observed pressure and temperature drop over the tubing and the production choke in an oil well.

The sensors in the production system constitute an integral part of the operating philosophy of the oil field and the work routines of the oil field operator. Therefore, it would be beneficial to be able to detect whether a sensor is trustworthy or whether it fails. A common approach to this question has been to define a set of allowable values for a particular sensor. Such an allowable set of values may be constant over time, e.g., the operator may specify a minimal and a maximal value. The allowable set may also depend on historical measurement data, e.g., the operator may specify a maximal rate of change. Unfortunately, it is often very difficult if not impossible to specify an allowable set of values. On the one hand, the set must have a limit that is small enough or sensitive enough to discriminate between correct and incorrect readings of a particular sensor other than those indicating complete failure of the equipment. On the other hand, the allowable set must have a range large enough to accommodate for a wide variety of possible operating conditions of the system, which can be considerable in number and extent.

Another problem related to failing sensors is that, unfortunately, it is often prohibitively expensive to replace such sensors by new ones. This is particularly true when the sensors are installed in remote locations in the production system, such as down in a well or on the bottom of the sea or other body of water. Therefore, it would also be beneficial to have a back-up value or reading available instead of the sensor itself for monitoring purposes when the sensor fails. A possible solution to this problem is to install multiple sensors of the same kind close to each other in the production system in order to obtain redundancy. In case any one of the sensors fails, one of the other sensors may be used to supply the data. This approach is costly and inefficient, since multiple sensors are involved to do the work of one. Another drawback of this approach is that such sensors of the same kind may be subject to the same errors due to the same well conditions.

SUMMARY OF INVENTION

The present invention provides a method performed in a data processing system for detecting sensor failure in an oil and gas production system. The method is performed under control of a set of computer-readable instructions contained in a computer program storage device. With the present invention, an expected value for a measurement from a sensor in the production system is generated. The expected value is compared against an actual measurement. If the expected value is within some acceptable specified limit of the actual measurement, the validity of the actual measurement is confirmed. If such is not the case, a failure of the sensor is indicated. The invention provides a model-based method for generating an expected, or back-up, value for a measurement from a specific sensor. This expected value is the value which is most consistent with the measurements from the other sensors in the system. The model used in the invention comprises descriptions of subsystems of the entire production system.

BRIEF DESCRIPTION OF THE DRAWINGS

FIG. 4 is a data plot showing a comparison between the down-hole pressure measured by a down-hole pressure sensor (gauge) and the corresponding estimated pressure according to an embodiment of the invention.

FIG. 5 is a schematic diagram of a directed graph representing an example oil and gas production system.

DESCRIPTION OF THE PREFERRED EMBODIMENT

Figure 1:
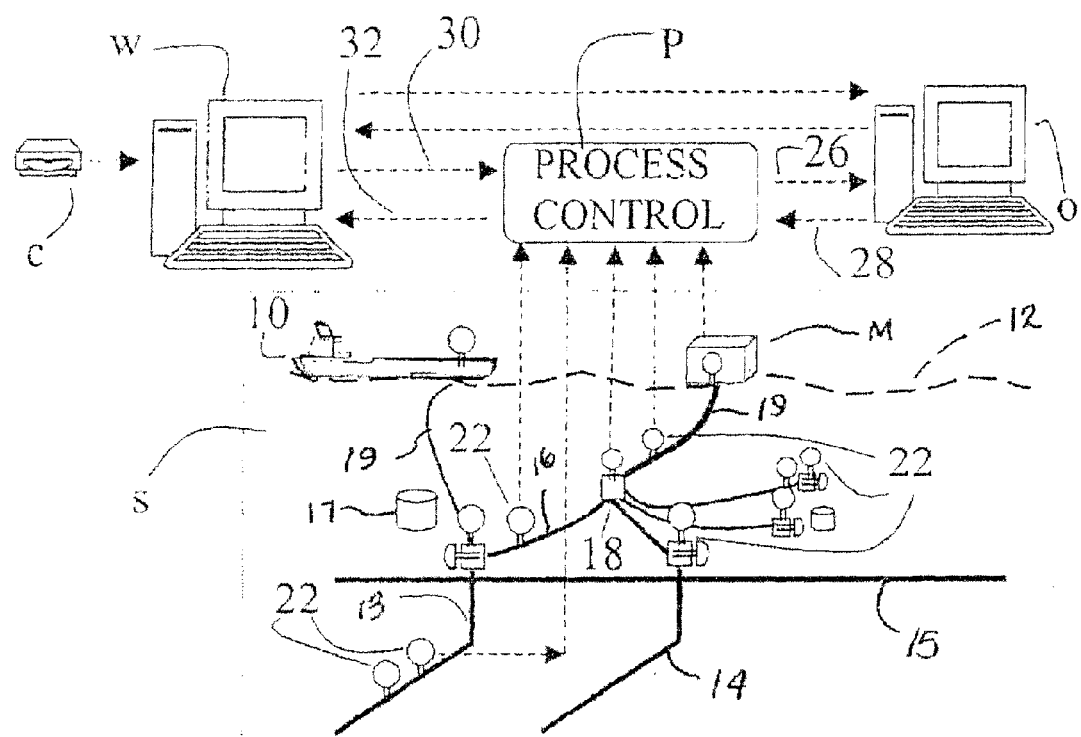
FIG. 1 is a schematic diagram of a typical offshore oil field in which the present invention is used.

In the drawings, an example oil and gas production system S is shown in FIG. 1. The system S contains the typical components of a production system for the production of oil and gas, such as wells, flowlines, manifolds, risers, and topside facilities, as well as systems for gas-lift and systems for the injection of chemicals. These elements comprise basic components for guiding, controlling, and observing the flow such as pipes, joints, bends, chokes, valves, pumps, separator tanks, heat exchangers, pressure gauges, temperature gauges, (multi-phase) flow meters, densitometers, and water cut meters.

The system S includes a production platform M in a body of water 12 connected to a set of wells, as shown schematically at 13 and 14 beneath a subsurface floor 15 in the body of water 12. The wells 13 and 14 are connected together through a set of flowlines 16, manifolds 18 and risers 19. The production system further contains a vessel 10 for the injection of chemicals. As is conventional, a number of sensors 22 are located in the production system S. Such sensors include pressure gauges, temperature gauges, multi-phase flow meters, densitometers, and water cut meters. These sensors are connected to a subsea control system or computer 17 which in its turn is connected to a topside control system or computer P.

The sensors 22 send readings or measurements as indicated schematically to a process control system or computer P operating under control of an operator station O and exchanging sensor readings and results as indicated schematically at 26 and 28. A well monitoring data processing system W in communication with the operator station O also exchanges instructions as indicated at 30 and receives sensor readings as indicated at 32 from the process control system O. The well monitoring system W and process control system P may be, for example, the Wellocate™ system of the type available from ABB, the assignee of the present application. According to the present invention, a computer program product C operating under a sequence of instructions described below causes the well monitoring data processing system W to monitor for failure of sensors 22.

Flow models in oil and gas production systems of the conventional type operate based on measurements obtained from the sensors 22. It is well known that the flow rate in an oil well may be found by measuring the pressure drop and/or the temperature drop over certain parts of the well and by identifying the flow rate that is most consistent with the measured pressure and/or temperature drop according to a model of the flow.

Figure 2:
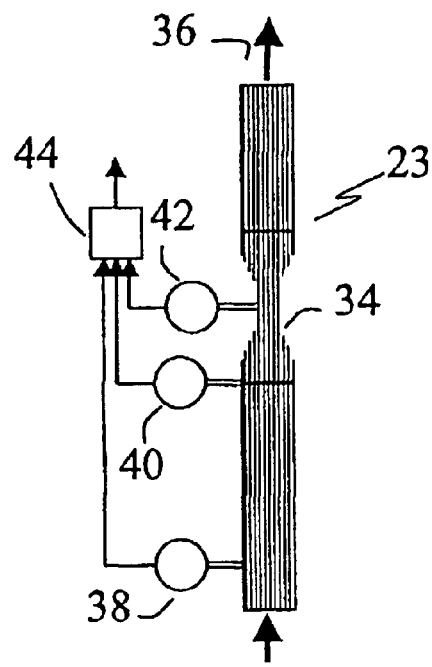
FIG. 2 is a schematic diagram of a venturi down-hole flow meter with on-board computing capability used in the oil field of FIG. 1.

An example of a sensor 22 in FIG. 1 may be a downhole model-based flow meter 23 shown schematically in FIG. 2. The flow meter 23 is available, for example, from the Expro International Group, PLC in the UK under the name SURE-FLO down-hole flow meter. The flow meter 23 includes a contracting tube (a Venturi tube) 34 inside tubing 36 in the production system S, and a down-hole pressure gauge 38. Pressure and temperature gauges 40 and 42 are located on both ends of tube 34. The down-hole flow meter 23 in FIG. 2 operates according to a model of the pressure drop over the Venturi tube 34 as a function of the flow rate (the Venturi equation). Further, such a down-hole flow meter 23 in FIG. 2 has an embedded computer 44 in order to facilitate certain calculations. Such a flow meter in FIG. 2 measures the pressure drop over the tube 34 and determines the flow rate by identifying the rate that is most consistent with the observed pressure drop according to the Venturi equation.

With the present invention a simulation is used to calculate previously unknown flow rates. The method of the present invention further uses those calculated flow rates to validate sensor measurements and further replace measurements from failed sensors in an oil and gas production system S.

Figure 3:
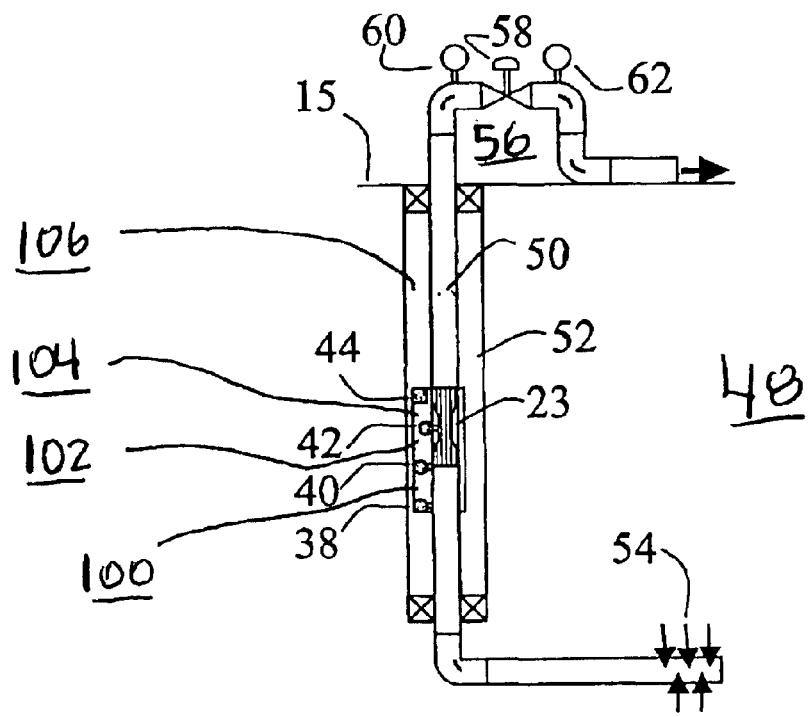
FIG. 3 is a schematic diagram of the venturi down-hole flow meter with on-board computing capability of FIG. 2 in place in an oil well.

A well 48 of the type in the production system S is shown in FIG. 3 including a tubing 50 contained in an annulus 52. Production enters the well 50 through the perforations in the inflow 54. On the well head 56 on the seabed 15 the production is contained by a production choke 58. The well is equipped with a down-hole venturi flow meter 23 as in FIG. 2, a well head pressure and temperature gauge 60 and a downstream pressure and temperature gauge 62. The down-hole flow meter is according to FIG. 2, including pressure/temperature gauges 38, 40, and 42 and a flow computer 44 for calculating the flow rate of oil and water.

Figure 6:
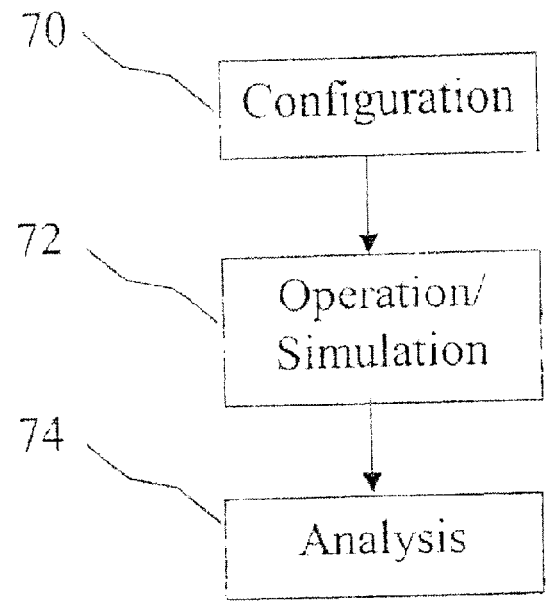
FIG. 6 is a flow chart indicating the basic steps of an operating sequence for detecting and correcting sensor failure in an oil and gas production system according to the present invention.

The present invention involves the following three phases as indicated schematically in FIG. 6.

Phase 1: Configuration: In the configuration phase 70 a user of the method of the present invention chooses and identifies which portion of the system S is to be monitored according to the present invention.

Phase 2: Simulation/Operation: In the simulation or operation phase 72 a number of steps are performed to obtain a simulated solution to the problem that the user has configured in configuration phase 70.

Phase 3: Analysis/Presentation: In the analysis or presentation phase 74 the results of the simulation or operation phase 72 are analyzed and presented to the user. It is in this phase that the system creates the most benefit for the user.

Phase 1: Configuration Phase:

In the configuration phase 70 the user of the invention sets up the problem which is to be solved. Configuration phase 70 according to the present invention involves choosing the following items in a group of steps:

1) The relevant part of the production system S under consideration for the problem at hand.
2) The number of distinguishable fluids of interest in the relevant part of the production system S selected in step 1).
3) For each of the fluids identified in step 2), a characterization of the composition.
4) For each of the fluids in step 2), an indication as to whether the flow rate of the fluid through the system S is a known variable, an unknown variable, or a function of an other variable in the system S.
5) The division of the relevant part of the production system S) selected in step 1) into a suitable number of subsystems for which elementary flow models exist.
6) For each of the subsystems selected in step 5), which flow model out of a set of possible flow models is to be used to best represent the behavior of the flow through the subsystem in question.
7) For each of the flow models chosen in step 6), which values for the model parameters are to be used so that the model best represents the behavior of the flow through the subsystem in question.

8) Which measured flow properties in the system S) are assumed a priori to be trustworthy, and which measured flow properties are assumed a priori to be flawed.

9) Which of the measured flow properties assumed a priori to be trustworthy in step 8) are to be subject to a consistency check by the present invention.

10) For each of the flow properties chosen in step 9), the specification of an interval to validate the measured flow property prior to the operation of the invention.

11) For each of the flow properties chosen in step 9), the specification of a test to determine whether the measured and the estimated flow property are consistent with each other or not.

12) Which of the measured flow properties assumed a priori to be flawed during step 8) are to be estimated by the present invention.

13) The point in time on which the system is supposed to operate.

These choices of steps 1) through 13) do not have to be made in the stated order as long as they are consistent with each other.

The relevant part of the production system S must be a connected subsystem of the production system S. Examples of such subsystems are a single oil well, a cluster with a number of wells, or the entire production system. Even though the present example is about the solution of a single problem in a single part of the production system S, it will be appreciated that the process of one or more instances of the present invention may be made concurrently in order to tackle various problems at the same time. Such multiple use of the invention may be seen as the repeated use of a single instance of the invention for a single problem as described in this example.

A preferred embodiment of the invention is embedded in an oil and gas production administrative system W, such as shown according to FIG. 1, which allows for the specification of a comprehensive production system from which connected subsystems may be selected for processing by the invention. The surrounding administrative system W also allows for repeated and parallel execution of multiple versions of the present invention.

Without loss of generality it is possible to identify at least one fluid of interest in the system S. To illustrate, it is customary in the oil industry to distinguish at least one oil (e.g., oil from a certain appraisal zone in the reservoir), possibly one or more gases (e.g., gas associated with the oil, free gas from a gas cap, injected lift gas), and possibly one water (e.g., an aquifer), from every well in an oil field.

In the preferred embodiment of the present invention a user defines a number of sources, that is, a number of points where fluids enter the production system S. Each of these sources allows for the specification of at most three distinguishable fluids, at most one oil, at most one gas, and at most one water.

There exist two common ways to describe the characterizing properties of such fluids:

1) The black oil fluid model distinguishes between oil, gas, and water. A fluid is described by means of the gas-oil-ratio and the water cut. The oil is characterized by its API gravity, the gas is characterized by its relative density, and the water is characterized by its density, all at standard conditions.

2) The compositional fluid model distinguishes between individual chemical components in the fluid. These components may be pure substances (e.g., methane, carbon dioxide) of which all relevant properties are known, or they may be hypothetical substances for which the density at standard conditions and the molecular weight is specified. The fluid is characterized by the mole fraction of the various components together with the fraction of water.

In the preferred embodiment of the present invention the compositional fluid model is used to describe the fluids of interest in the production system. There are a number of models based on an equation of state that describe the physical properties of flow characterized by a compositional fluid model. In the preferred embodiment of the invention the model by Peng and Robinson (R. C. Reid, J. M. Prausnitz, B. E. Poling, The Properties of Gases & Liquids, McGraw-Hill Book Co, 1988) is used to calculate such flow properties.

A user is in principle free to choose which flow rates are unknown variables to be determined by the invention in operation or simulation phase 72 and which flow rates are known variables or functions of other variables. To illustrate the foregoing, it is typical in the oil industry to assume that the rate of oil from a well is either an unknown variable, or a function of the difference in pressure between the reservoir and the down-hole pressure in the well bore, and, as such, a function of an other variable in the system, the down-hole pressure. To give another example, it is typical to assume at least in the short term that the rate of gas in an oil well without a gas cap is a constant fraction of the rate of oil.

It is important to note that there typically is a limit on the total number of unknown variables that the present invention can estimate in operation or simulation phase 72, based on the total number of independent, trustworthy measured flow properties identified in step 8) as previously described.

For all relevant components in an oil production system S such as shown in FIG. 1, there is at least one model available in the literature to describe the flow through the component with a certain degree of accuracy, based on the granularity of the division of the system into subsystems. The optimal model of a production system is the one with a minimal number of subsystems that provides an acceptable degree of accuracy for the range of expected flow conditions.

The measurements assumed a priori to be trustworthy are the known reference points for the simulation in phase 2. It is important that there are enough of such reference points.

Phase 2: Simulation/Operation Phase

The operation phase 72 is composed of three steps:

Step 1: Data Collection: In the Data Collection step of the simulation/operation phase 72, data from the sensors 22 in the relevant part of the production system S selected in the configuration phase 70 is collected for the point in time selected in the configuration phase 70.

Step 2: Data Validation: In the Data Validation step of the simulation/operation phase 72, the measured data is validated according to the a priori rules for validation of data that the user has selected in the configuration phase 70. As a result of this data validation step, a flag is set for all sensors in the selected part of the production system S indicating whether the associated measured physical property of the flow is believed to be valid prior to operation of the invention.

Step 3: Simulation: In the Simulation step of the simulation/operation phase 72, the flow in the selected subsystem is simulated at the selected point in time on the basis of the collected data by using the constituted simulation model of the production system. In the simulation step of operation phase 72 the present invention determines the value of relevant flow properties in the relevant part of the production system S, based on the choices made in phase 70.

Simulating the flow in the production system S is in effect knowing the value of all the relevant properties of the flow through the system. Without loss of generality, it suffices to know a set of characterizing properties of the flow, that is, a set of basic properties of the flow from which all other properties may be derived by means of models. In the preferred embodiment of the present invention, track is kept of the pressure, the temperature, the flow rate, and the composition of the flow. It should be noted that this is merely one possible set of characterizing properties: another characterizing set would be the pressure, the enthalpy, the flow rate, and the composition of the flow.

For practical applications, it is only necessary to know flow properties in a limited number of selected locations in order to obtain an impression of the behavior of the flow everywhere in the system. Therefore in the preferred embodiment of the invention the simulation phase estimates the characterizing flow properties at the inlet and at the outlet of every subsystem of the production system identified during the configuration phase 70.

In the preferred embodiment of the present invention the production system is represented as a directed graph, where the edges represent the basic flow containing components, where the direction of the edges represents the designated direction of flow, and where the vertices represent the components where the flow containing components are linked together as well as the locations of the sensors in the system. The locations where flow enters the system or where it flows out of the system, known as sources and sinks in graph theory, are also represented as vertices.

In the preferred embodiment of the present invention the relevant part of the production system is represented as a directed graph for the purpose of the simulation portion of phase 72. The following elements in the relevant part of the production system S are represented in a directed graph:

1. the sources, that is, the locations where fluids flow into the system;
2. the sinks, that is, the locations where fluids flow out of the system;
3. the manifolds, that is, the locations where more than one flow get commingled;
4. the routers and separators, that is, the locations where the flow is split into more than one flow; and
5. the sensors, that is, the locations where at least one flow property is being measured.

FIG. 5 shows a directed graph G representing an oil and gas production system. The main structure of a directed graph such as shown in FIG. 5 includes leaves 80, nodes 82, branches 84, and a root 86. The leaves 80 in directed graph tree of FIG. 5 represent the sources in the oil and gas production system S, that is, points where oil and gas enters the production system S. A source may be an inflow, that is, a hole in the tubing down in a reservoir through which oil/gas enters the production network. It may be an inlet into a pipeline with a given pressure and/or flow rate. A source may also be a gas injection point in a gas-lifted well, as well as other locations of inflow into various types of wells. The word source must be read in the designed direction of flow, since there are circumstances where production flows back from the production facilities into a source. The direction of flow of the oil and gas from the sources to a separator is represented by the direction in the tree from the leaves to the root.

Nodes 82 in the directed graph tree of FIG. 5 may represent reference points and further represent what are known as manifolds in the oil industry. A manifold is a blending point where the flow from a number of inlet flow lines comes together and continues its way through a single outlet flow line. A reference point is a point where some piece of information is available, such as a measured value of the pressure, the temperature, or the flow rate, or some constant value, such as the pressure in a separator.

A branch 84 in directed graph G represents the flow lines that comprise a sequence of pipes and chokes. The root 86 is the most downstream node in the network, in the sense that all production eventually arrives to the root. The root in a directed graph which describes an entire oil and gas production system typically represents an inlet to a separator.

The edges in the directed graph G of FIG. 5 represent the basic flow containing components in between these vertices and the direction of the edges indicates the designated direction of flow.

There is a unique directed graph associated with any production system, but it should be understood that the use of a directed graph is not the only method available to build a model suitable for simulation according to the present invention of the production system S.

In the preferred embodiment of the present invention, the production system S is modeled as a linked list of components which is derived from a directed graph. Each component is modeled as a list of parameters of the component. Such sets of parameters refer to elementary models of such components that are available to the system in the form of a library of models. There are many ways to model flow in elementary flow containing components such as pipes and chokes. The preferred embodiment of the invention contains common models such as:

a mechanistic model for pressure drop in pipes based on mass, energy, and momentum balances, as described in the previously mentioned paper entitled" "Oil Well Allocation: the Ultimate Interpolation Problem,"

a mechanistic model for the pressure drop in chokes known as the Perkins model, as described in the previously mentioned paper entitled "Oil Well Allocation: the Ultimate Interpolation Problem,"

a heat transfer model between the flow in pipes and the environment based on an overall heat transfer coefficient, as described in the previously mentioned paper entitled "Oil Well Allocation: the Ultimate Interpolation Problem,"

It is important to note that these models are examples of models that describe the behavior of flow in elementary flow containing components and that they may be replaced by other models from the literature or devised on the basis of experiments on the equipment. It is also important to note that for many of the physical processes involved there is no such thing as an exact model since the processes are too complicated to be fully understood. However, the available models in the literature, including the models mentioned above, have shown to be reasonably accurate and at least accurate enough for the purpose of this invention.

In the simulation step of operation phase 72, the present invention tries and solves a system of equations in order to find previously unknown properties of the flow on the basis of previously known properties of the flow. There are many ways to solve such a system of equations. The following is a description of the preferred embodiment of the invention.

The variables in the system are the pressure, the temperature, the flow rate, and the composition of the flow in all the vertices of the directed graph that represents the production system. The equations that need to be observed are the physical models for pressure and temperature drop over the edges of the graph as described above. In addition there are a large number of what is known as constitutional relations in the graph:

The pressure in all edges into and out of a vertex is identical.

The flow out of a vertex is the sum of the flows into a vertex.

Figure 7:
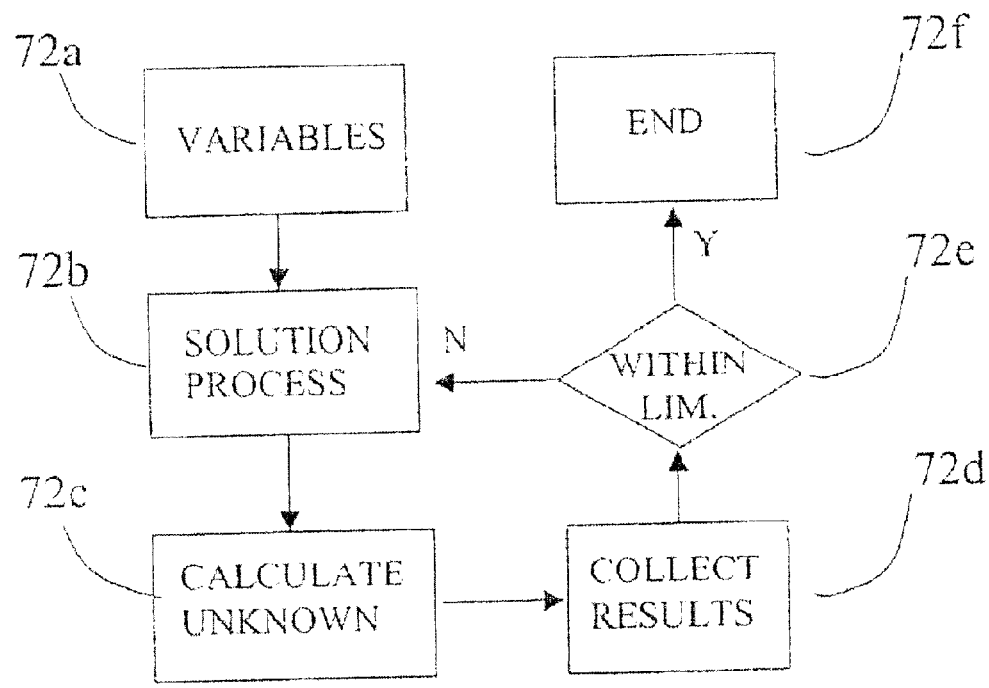
FIG. 7 shows a flow chart of steps performed by a data processing system implementing the second basic step of the present invention of FIG. 6.

The main steps in the simulation step 72 are as follows (see FIG. 7):

1. During a step 72a, some of the variables are known due to measurements that have been validated, other variables are unknown.
2. Next, during step 72b, a solution process or technique performed in the data processing system as described below assumes the value of some of the unknowns, such as the flow rates from all the sources and the pressure in all the vertices.
3. Then, during step 72c, the unknowns in the graph are calculated in the direction of the graph on the basis of known values and the available models.
4. During step 72d, when all unknowns are known in this iteration step, the mismatches between calculated values and values that were known due to measurements, as well as the mismatch between calculated values and the constitutional relations in the graph are collected and assembled.
5. If these mismatches are determined to be under a pre-specified level during step 72e, the simulation is done as indicated at step 72f. Otherwise the mismatch is used by the solution technique to assume better values and start over in step 72b.

The computation of the calculated values is based on a system of ordinary differential equations (ODE's) describing the behavior of the pressure and the temperature along a pipe with a multi-component, multi-phase fluid. In addition, models for the change in pressure and temperature across other equipment such as venturi down-hole flow meters and chokes are evaluated. The ODE's are non-linear and they are based on conservation of energy, mass, and momentum along the pipe. Evaluation of the derivatives defining the ODE's involves thermodynamic equilibrium calculations for each fluid component at each integration point along the pipe. Integration of the ODE's along the pipes, together with evaluation of the models for the rest of the equipment, gives the pressure, the temperature, and other physical quantities like velocities, densities, and viscosities at all points of interest in a fluid transport pipe network.

The preferred embodiment of the invention uses a state-of-the-art solution technique for a system of nonlinear equations. A state of the art method for the solution of nonlinear least-squares problems is for example the Levenberg-Marquardt method. Techniques of this type are described, for example, in the following literature:

1. Marquardt, D. (1963), "An algorithm for least-squares estimation of nonlinear parameters, SIAM Journal on Applied Mathematics", 11, 431–441.
2. Dennis, J. E., Jr., and Robert B. Schnabel (1983), Numerical Methods for Unconstrained Optimization and Nonlinear Equations, Prentice-Hall, Englewood Cliffs, N.J.
3. Gill, Philip E., Walter Murray, and Margaret Wright (1981), Practical Optimization, Academic Press, New York.

Phase 3: Analysis/Presentation Phase

The Presentation or Analysis Phase 74 includes in general several actions. For the available sensors, the mismatch is registered between the simulated and the measured value of the property of the flow. For all unavailable sensors, the simulated value is registered in order to replace the unavailable measured value of the property of the flow.

In the analysis phase 74, the simulated flow properties obtained during operation phase 72 are compared with the measured flow properties selected in configuration phase 70. This is done in order to check the consistency of these measured flow properties. In the analysis phase 74 a method according to the present invention also supplies estimated flow properties. Those flow properties are results of simulations made in phase 72 as a replacement of the results from the failed sensors indicated in configuration phase 70.

Figure 8:
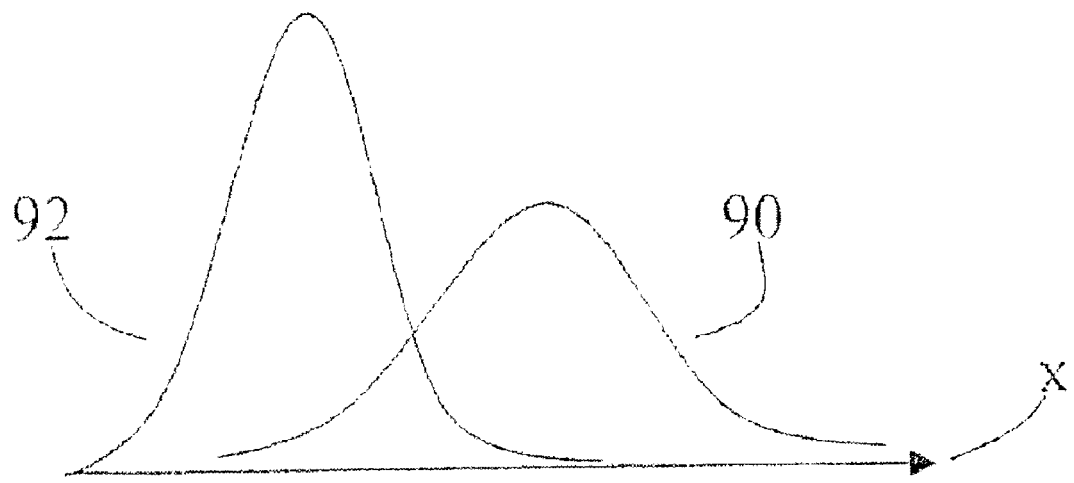
FIG. 8 is an example of a graph showing a probability distribution for a calculated sensor value and a probability distribution for the corresponding measured sensor value.

This supplying of estimated flow properties is done according to the present invention based on probability distribution of measurement values and model parameters for the sensors. FIG. 8 shows an example of a graph representing probability distribution of a sensor, such as the devices described above in the production system S. Such devices measure any of the following properties of a fluid inside a pipe or any other pressure containing equipment: absolute pressure, differential pressure (e.g. used in venturi tubes), temperature, density (e.g. nucleonic densitometers), phase fractions (e.g. fluid dielectricity, capacitance and impedance meters), molecular compositions, salinity (e.g. with conductivity meters and or nucleonic densitometers), velocity and momentum.

The detection of sensor error according to the present invention is based on a comparison of the probability distribution of the value for the calculated sensor value (calculated during the simulation phase 72) with the probability distribution of the measured sensor value. This is illustrated in FIG. 8 which is an example with normal distributions for both. The wider probability distribution indicated at 90 is the calculated value during the simulation phase 72, while the more narrow distribution indicated at 92 is the probability distribution for the sensor to be validated.

An important observation to make at this point is that the definition of a probability distribution or confidence interval for the deviation between an estimated flow property and a measured flow property is a completely different task than the definition of a confidence interval for the measured flow property as such, as is done in the prior art. It is to be expected that an educated guess of a certain flow property based on trustworthy observations is a considerably more selective benchmark, hence, that the confidence interval for the deviation is typically much smaller than the confidence interval required for the measured flow property as such. One example of a criterion for valid sensor is that the "union area" is larger than a certain limit.

The probability distribution 90 of the calculated sensor value is found with the present invention by performing multiple simulations with the process simulation model for the sensors other than the test sensor to validated, which is not used for the simulation. The process simulation model measured sensor values with a probability distribution (error) added to each sensor and using model parameters with errors added to each of the main model parameters. The probability distribution 92 of the measured value for each sensor is defined or may be obtained from the data available from the vendor of the particular sensor.

In a preferred embodiment the present invention also defines and presents the expected error distribution for a back-up value of a sensor based on a calculated error distribution. This is done by what can be termed validating a sensor model parameter.

It can be assumed that every sensor and every model parameter has a known variance. Then the variance of the simulated value or soft sensor value can be estimated. Once these variances are known any sensor may be validated.

For this purpose, one can define $$y = u - m,$$

where u is the simulated value and m is the measured value from the sensor which is to be tested. The variance of y is then $$Var(y) = Var(u) + Var(m)$$

since the simulated value u and the measured value m are uncorrelated. A further assumption is that both the simulated value and the measured value are distributed according to a Gauss probability function. In that case one may perform the following validation test:

Let the result of a specific measurement and the corresponding simulation be $$u = u_0$$
$$m = m_0$$
$$y = y_0 = u_0 - m_0.$$

Let $P_0$ be the probability that the values are as above or more extreme ($|y| > |y_0|$), given that the expected value of y is zero (in which case the expected value for u and m is the same), $$P_0 = P(|y| > |y_0| | E(y) = 0).$$

The sensor cannot be trusted if $P_0 < \alpha$, where $\alpha$ is chosen in advance. A typical choice would be $\alpha = 5\%$, in which case the sensor would be rejected if $|y_0| \geq 2*\sqrt{Var(y)}$.

Computing the Variance of the Simulated Value

Let u be the simulated or back-up value obtained with the model parameters and sensor values $\alpha_1, \ldots, \alpha_n$. All these values have known accuracies, given by their variance. The variance (which is the square of the standard deviation) of sensor (or model parameter) $\alpha$, is denoted by $Var(\alpha_1)$. The simulated value may be written as some function of the parameters, i.e.

$$u = f(\alpha_1, \ldots, \alpha_n).$$

For a given set of parameters let the simulated value be denoted by $u_0$, $$u_0 = f(\alpha_1^*, \ldots, \alpha_n^*).$$

Assume that locally u can be well approximated by a linear function such that $$u \approx C + \sum_{i=1}^{n} x_i a_i,$$

where $x_i$ are coefficients to be determined. By perturbing one parameter at a time the unknown coefficients can be estimated in the following way:

$$u_0 \approx C + x_1 a_1^* + \sum_{i=2}^{n} x_i a_i^*$$

$$u_1 \approx C + x_1 (a_1^* + \varepsilon_1) + \sum_{i=2}^{n} x_i a_i^*.$$

Subtracting the two equations gives $$u_1 - u_0 \approx x_1 \varepsilon_1,$$

from which $x_1$ may be found. This means that the coefficients are the partial derivatives of f with respect to each of the variables, i.e.

$$x_i = \left. \frac{\partial f}{\partial a_i} \right|_{a_i = a_i^*}.$$

Once the coefficients are determined, the variance of the simulated value is found in a standard way as $$Var(u) \approx \sum_{i=1}^{n} x_i^2 Var(a_i).$$

If a certain sensor value is evaluated as being unreliable the calculated sensor value is used as back-up value. The back-up value can be sent to the control system to be used for control purposes or optimization.

EXAMPLE ON CASE

As an example result, the foregoing analysis was performed on a sensor layout of the type shown in FIG. 3. The relevant part of the production system S in this example runs from the pressure and temperature gauge 38 down-hole in FIG. 3 to the well head pressure and temperature gauge 60 in FIG. 3.

In this example there is only one relevant fluid flowing through the well, an oil with an unknown flow rate and a known composition.

The relevant part of the production system S is subdivided into the following subsystems;

a lower tubing 100 from the down-hole sensor 38 to the inlet of the venturi 40 in FIG. 3;

a venturi inlet tube 102 from the gauge 40 to the gauge 42 in FIG. 3;

a venturi outlet tube 104 from the gauge 42 to the top of the venturi downhole flow meter 23 in FIG. 3; and an upper tubing 106 from the top of the venturi downhole flow meter 23 to the gauge 60 in FIG. 3 in the well consisting of a number of pipe segments with different properties.

The measured flow properties in the relevant part of the production system are (a) the pressure at the inlet to the venturi 40;

(b) the temperature at the inlet to the venturi 40;

(c) the pressure inside the venturi 42;

(d) the temperature inside the venturi 42;

(e) the flow rate of oil through the venturi;

(f) the pressure on the well head 60;

(g) the temperature on the well head 60;

A priori we assume that all of these properties are trustworthy. In addition we measure the downhole pressure 38 but we assume that this pressure is untrustworthy.

The flow rate of oil (e) is subject to a consistency check by the invention. This means that we use the invention to calculate (simulate) the flow rate of oil and then check whether the measured flow rate of oil (e) is consistent with the calculated flow rate of oil.

We also use the invention to check whether the downhole pressure is valid or not and we provide a backup value for the down-hole pressure in cases where it is not valid.

FIG. 4 shows a comparison between the measured downhole pressure 65 and the calculated downhole pressure 66 according to an embodiment of the invention. It is obvious that the sensor is severely flawed since measurements are only available at some point in time. The results show that the estimated pressure is very close to the measured pressure at times when the measured pressure is available. The estimated pressure provides a reliable back-up value for the down-hole pressure measurement at times when the sensor is not available.

The foregoing disclosure and description of the invention are illustrative and explanatory thereof, and various changes in the size, shape, materials, components, processing and computational steps and procedures, as well as in the details of the illustrated circuitry and construction and method of operation may be made without departing from the spirit of the invention.

What is claimed is:

1. A method for detecting sensor failure in an oil and gas production system, comprising performing in a data processing system:

generating from a process model of the oil and gas production system using measurements from one or more sensors an expected value for a sensor measurement;

comparing the expected value with an actual measurement obtained from a first sensor in said oil and gas production system;

if the expected value is within acceptable specified limits of the actual measurement confirming the validity of the actual measurement obtained; and if the expected value is not within acceptable specified limits of the actual measurement, indicating the failure of the sensor and replacing the value of the actual measurement with the expected value.

2. The method of claim 1, wherein said generating an expected value for a sensor measurement comprises performing in a data processing system obtaining a probability distribution of expected values for the sensor measurement.

3. The method of claim 2 wherein said obtaining of a probability distribution of expected values comprises performing in a data processing system multiple simulations of the oil and gas production system using sensors in the production system other than the first sensor over a range of possible sensor readings from the other sensors.

4. The method of claim 3 wherein said obtaining of a probability distribution of expected values comprises performing in a data processing system multiple simulations of the oil and gas production system using a range of model parameters for the production system.

5. The method of claim 1, wherein a probability distribution of measured sensor values is available and said comparing comprises performing in a data processing system obtaining a probability distribution of the difference between the expected value and the actual measurement obtained from the sensor.

6. The method of claim 5, wherein said comparing comprises performing in a data processing system obtaining the acceptable specified limits for the difference between the expected value and the actual measurement by means of said probability distribution of the difference between the expected value and the actual measurement.

7. A method for detecting sensor failure in an oil and gas production system, comprising the steps performed in a data processing system:

generating an expected value for a sensor measurement from a process model of the oil and gas production system, by means of one (or more) generated back-up value(s), the back-up value(s) primarily being generated by means of the process model;

comparing the expected value with an actual measurement obtained from a first sensor in said oil and gas production system;

if the expected value is within acceptable specified limits of the actual measurement confirming the validity of the actual measurement obtained; and if the expected value is not within acceptable specified limits of the actual measurement, indicating the failure of the sensor and replacing the value of the actual measurement with the expected value.

8. The method of claim 7, wherein said generating an expected value for a sensor measurement comprises performing in a data processing system obtaining a probability distribution of expected values for the sensor measurement.

9. The method of claim 8 wherein said obtaining a probability distribution of expected values comprises performing in a data processing system multiple simulations of the oil and gas production system using sensors in the production system other than the first sensor over a range of possible sensor readings from the other sensors.

10. The method of claim 9 wherein said obtaining a probability distribution of expected values comprises performing in a data processing system multiple simulations of the oil and gas production system using a range of model parameters for the production system.

11. The method of claim 7, wherein a probability distribution of measured sensor values is available and said comparing comprises performing in a data processing system obtaining a probability distribution of the difference between the expected value and the actual measurement obtained from the sensor.

12. The method of claim 11, wherein said comparing comprises performing in a data processing system obtaining the acceptable specified limits for the difference between the expected value and the actual measurement by means of said probability distribution of the difference between the expected value and the actual measurement.

13. A computer program product for causing a data processing system to monitor for sensor failure in an oil and gas production system, the computer program product comprising:

a computer program storage device;

computer-readable instructions on the storage device for causing the data processing system to monitor for sensor failure in the oil and gas production system by performing:

generating from a process model of the oil and gas production system using measurements from one or more sensors an expected value for a sensor measurement;

comparing the expected value with an actual measurement obtained from a first sensor;

if the expected value is within acceptable specified limits of the actual measurement confirming the validity of the actual measurement obtained; and if the expected value is not within acceptable specified limits of the actual measurement, indicating the failure of the sensor and replacing the value of the actual measurement with the expected value.

14. The computer program product of claim 13, wherein the computer-readable instructions further include instructions for causing the data processing system to perform obtaining a probability distribution of expected values for measurement from the sensor.

15. The computer program product of claim 13, wherein the computer-readable instructions further include instructions for causing the data processing system to perform multiple simulations of the production system using sensors in the production system other than the first sensor over a range of possible sensor readings from the other sensors.

16. The computer program product of claim 13, wherein the computer-readable instructions further include instructions for causing the data processing system to perform obtaining a probability distribution of the difference between the expected value and the actual measurement obtained from the sensor.

17. The computer program product of claim 16, wherein the computer-readable instructions further include instructions for causing the data processing system to perform obtaining the acceptable specified limits for the difference between the expected value and the actual measurement by means of said probability distribution of the difference between the expected value and the actual measurement.

18. A computer program product for causing a data processing system to monitor for sensor failure in an oil and gas production system, the computer program product comprising:

a computer program storage device;

computer-readable instructions on the storage device for causing the data processing system to monitor for sensor failure in the oil and gas production system by:

generating an expected value for a sensor measurement from a process model of the oil and gas production system, by means of one (or more) generated back-up value(s), the back-up value(s) primarily being generated by means of the process model;

comparing the expected value with an actual measurement obtained from a sensor in said oil and gas production system;

if the expected value is within acceptable specified limits of the actual measurement confirming the validity of the actual measurement obtained; and if the expected value is not within acceptable specified limits of the actual measurement, indicating the failure of the sensor and replacing the value of the actual measurement with the expected value.

19. The computer program product of claim 18, wherein the computer-readable instructions further include instructions for causing the data processing system to perform obtaining a probability distribution of expected values for measurement from the sensor.

20. The computer program product of claim 18, wherein the computer-readable instructions further include instructions for causing the data processing system to perform multiple simulations of the production system using a range of model parameters for the production system.

21. The computer program product of claim 18, wherein the computer-readable instructions further include instructions for causing the data processing system to perform obtaining a probability distribution of the difference between the expected value and the actual measurement obtained from the sensor.

22. The computer program product of claim 21, wherein the computer-readable instructions further include instructions for causing the data processing system to perform obtaining the acceptable specified limits for the difference between the expected value and the actual measurement by means of said probability distribution of the difference between the expected value and the actual measurement.

* * * * *